(12) United States Patent
Ookouchi et al.

(10) Patent No.: US 10,197,568 B2
(45) Date of Patent: Feb. 5, 2019

(54) BASE MATERIAL COMPRISING HYDROPHILIC LAYER

(75) Inventors: Norihiko Ookouchi, Tokyo (JP); Hirohito Ayame, Tokyo (JP); Yuichi Tanaka, Tokyo (JP); Hiroko Watanabe, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 575 days.

(21) Appl. No.: 14/130,047

(22) PCT Filed: Apr. 16, 2012

(86) PCT No.: PCT/JP2012/060222
§ 371 (c)(1),
(2), (4) Date: Dec. 30, 2013

(87) PCT Pub. No.: WO2013/001894
PCT Pub. Date: Jan. 3, 2013

(65) Prior Publication Data
US 2014/0193302 A1    Jul. 10, 2014

(30) Foreign Application Priority Data
Jun. 28, 2011   (JP) .................................. 2011-143259

(51) Int. Cl.
*G01N 33/543*    (2006.01)

(52) U.S. Cl.
CPC . *G01N 33/54393* (2013.01); *G01N 33/54353* (2013.01)

(58) Field of Classification Search
CPC .................. G01N 33/54353; G01N 33/54393
See application file for complete search history.

(56) References Cited

U.S. PATENT DOCUMENTS

| | | | |
|---|---|---|---|
| 6,113,906 A * | 9/2000 | Greenwald | ...... A61K 47/48215 424/178.1 |
| 7,097,882 B2 | 8/2006 | Seo et al. | |
| 8,367,213 B2 | 2/2013 | Nishimi et al. | |
| 8,497,106 B2 | 7/2013 | Suarez | |

(Continued)

FOREIGN PATENT DOCUMENTS

| | | |
|---|---|---|
| EP | 1202063 A1 | 5/2002 |
| JP | 11-264823 A | 9/1999 |

(Continued)

OTHER PUBLICATIONS

International Search Report of International Application No. PCT/JP2012/06022 dated May 22, 2012.

*Primary Examiner* — Michael B Nelson
(74) *Attorney, Agent, or Firm* — McCarter & English, LLP

(57) ABSTRACT

This invention provides a base material comprising a plastic-containing support and, on its surface, a hydrophilic layer comprising an ethylene glycol chain (an EG chain) composed of one or more ethylene glycol units, as well as a method for producing such base material. A polysiloxane-containing primer layer is provided on the support comprising a plastic material on its surface, and the EG chain is covalently bound to a polysiloxane side chain of the primer layer. Thus, a hydrophilic layer comprising the EG chain can be provided on the surface of the plastic-containing support.

2 Claims, 14 Drawing Sheets

(56) References Cited

U.S. PATENT DOCUMENTS

| | | | |
|---|---|---|---|
| 2002/0018860 A1* | 2/2002 | Filippou | B05D 3/08 427/532 |
| 2003/0104397 A1* | 6/2003 | Lefkowitz | G01N 33/54393 435/6.11 |
| 2004/0110276 A1 | 6/2004 | Amontov et al. | |
| 2004/0185260 A1* | 9/2004 | Luzinov | B05D 1/38 428/413 |
| 2005/0271810 A1* | 12/2005 | Kobrin | B05D 1/60 427/248.1 |
| 2005/0287560 A1 | 12/2005 | Garimella et al. | |
| 2006/0263793 A1 | 11/2006 | Lee et al. | |
| 2008/0131978 A1 | 6/2008 | Fujimura et al. | |

FOREIGN PATENT DOCUMENTS

| | | |
|---|---|---|
| JP | 2003-177129 A | 6/2003 |
| JP | 2005-164348 A | 6/2005 |
| JP | 2006-509201 A | 3/2006 |
| JP | 2006-143715 A | 6/2006 |
| JP | 2007-078399 A | 3/2007 |
| JP | 2008-107310 A | 5/2008 |
| JP | 2009-515138 A | 4/2009 |
| JP | 4648944 B2 | 3/2011 |
| WO | WO-2005/075997 A1 | 8/2005 |
| WO | WO-2007/069608 A1 | 6/2007 |

\* cited by examiner

Plate of the present invention　　　　　　Untreated plate

Fig. 14

| Hydrophilic compound | Duration of silanol treatment Number average molecular weight (Number average molecular weight of raw material-18) | 60 min N/C-O | 60 min Sensitivity (ng/ml) | 75 min N/C-O | 75 min Sensitivity (ng/ml) | 90 min N/C-O | 90 min Sensitivity (ng/ml) | 105 min N/C-O | 105 min Sensitivity (ng/ml) | 120 min N/C-O | 120 min Sensitivity (ng/ml) | 135 min N/C-O | 135 min Sensitivity (ng/ml) |
|---|---|---|---|---|---|---|---|---|---|---|---|---|---|
| EG | 44 | 0.413 | | 0.584 | | 0.292 | | 0.197 | | 0.164 | 15.6 | 0.152 | |
| Di EG | 88 | 0.611 | | 0.484 | | 0.253 | | 0.176 | | 0.132 | 7.8 | 0.127 | |
| Tri EG | 132 | 0.345 | 7.8 | 0.290 | 7.8 | 0.219 | 3.9 | 0.148 | 3.9 | 0.121 | 3.9 | 0.118 | 7.8 |
| Tetra EG | 176 | 0.258 | 3.9 | 0.298 | 3.9 | 0.188 | 0.49 | 0.128 | 0.12 | 0.100 | 0.03 | 0.096 | 0.03 |
| PEG400 | 362~402 | 0.160 | 1.0 | 0.163 | 1.0 | 0.127 | 1.0 | 0.081 | 0.06 | 0.060 | 0.03 | 0.065 | 0.03 |
| PEG600 | 552~612 | 0.200 | | 0.217 | | 0.141 | | 0.059 | | 0.049 | 0.03 | 0.048 | |
| PEG1000 | 932~1032 | 0.129 | 0.12 | 0.112 | 0.12 | 0.075 | 0.06 | 0.046 | 0.03 | 0.043 | 0.03 | 0.043 | 0.03 |
| PEG1540 | 1282~1582 | 0.121 | 0.49 | 0.120 | 0.24 | 0.181 | 0.24 | 0.028 | 0.03 | 0.036 | 0.03 | 0.039 | 0.06 |
| PEG2000 | 1832~2132 | 0.177 | 0.12 | 0.086 | 0.06 | 0.070 | 0.06 | 0.043 | 0.03 | 0.035 | 0.03 | 0.039 | 0.03 |
| PEG4000 | 2682~3382 | 0.114 | 0.24 | 0.107 | 0.24 | 0.087 | 0.06 | 0.041 | 0.03 | 0.038 | 0.03 | 0.030 | 0.03 |
| PEG6000 | 7282~10182 | 0.109 | | 0.099 | | 0.089 | | 0.033 | | 0.044 | 0.03 | 0.033 | |
| PEG10000 | 8982~12482 | 0.096 | 0.03 | 0.061 | 0.03 | 0.038 | 0.03 | 0.045 | 0.03 | 0.030 | 0.06 | 0.029 | 0.03 |
| PEG20000 | 14982~24982 | 0.083 | 0.03 | 0.050 | 0.03 | 0.055 | 0.03 | 0.049 | 0.03 | 0.048 | 0.03 | 0.044 | 0.03 |

Bold: High sensitivity (sensitivity: 0.06 ng/ml or lower)

EG: ethylene glycol; Di EG: diethylene glycol; Tri EG: triethylene glycol; Tetra EG: tetraethylene glycol

BASE MATERIAL COMPRISING HYDROPHILIC LAYER

RELATED APPLICATIONS

This application is a national stage application filed under 35 USC 371 of PCT/JP2012/060222, filed Apr. 16, 2012, which claims the benefit of Japanese Patent Application No. 2011-143259, filed Jun. 28, 2011, all of which are incorporated herein, in entirety, by reference.

TECHNICAL FIELD

The present invention relates to a base material comprising a hydrophilic layer on its surface, which is useful as a material constituting a test device or the like.

BACKGROUND ART

Enzyme-linked immunosorbent assay (ELISA), which is a type of immunoassay technique, has been utilized in a wide variety of industries, including the drug discovery, diagnosis, environmental measurement, and food industries. Typically, ELISA comprises 5 steps: (1) fixation of antibodies or antigens (solid-phase formation); (2) binding of target substances; (3) binding of enzyme-labeled antibodies; (4) enzyme reactions; and (5) optical detection (absorption, fluorescence, or luminescence detection). As enzyme labels, horseradish peroxidase, alkaline phosphatase, and the like are used. Among many immunoassay techniques, ELISA is carried out with a particularly high sensitivity. In fact, however, sensitivity is often not as high as expected due to nonspecific adsorption of biomolecules to a solid-phase carrier. In particular, a complex such as an enzyme-labeled antibody is likely to adsorb to a solid-phase carrier, and such adsorption is a primary cause for noise in ELISA. In order to prevent such nonspecific adsorption, a carrier may be blocked with bovine serum albumin (BSA), although the effects thereof are limited. Accordingly, polyethylene glycol (PEG), which effectively prevents nonspecific adsorption of biomolecules, has drawn attention. Specifically, it allows antibodies or antigens to be fixed to a carrier with the aid of PEG linkers, so as to prevent nonspecific adsorption of biomolecules to the solid-phase carrier.

Patent Document 1 discloses a method of fixing an antibody onto a gold surface via a PEG linker. Specifically, a nonionic functional group is introduced onto the gold surface, one end of a heterobifunctional PEG is covalently bound thereto, and an antibody is bound to the other end. Patent Document 1 describes that noise generated by the surface plasmon resonance technique can be reduced to a significant degree with such technique.

Patent Document 2 discloses a technique in which a nucleic acid or protein is fixed onto a glass surface via a PEG linker. Specifically, a silane compound having a PEG linker is synthesized, the resulting compound is applied to a glass surface, and a nucleic acid or protein is bound to an end of the PEG linker. Patent Document 2 describes that the signal-to-noise (S/N) ratio (i.e., sensitivity) of a biochip is improved by such technique.

Patent Document 3 discloses a technique in which a nucleic acid is fixed onto a glass surface via a PEG linker. Specifically, an amino group is introduced onto a glass surface with the aid of a silane coupling agent, one end of a homobifunctional PEG is covalently bound thereto, and a nucleic acid is bound to the other end. Patent Document 3 describes that the sensitivity of a biosensor is improved by such technique.

Meanwhile, various biochemical tests, such as immunoassays, often involve the use of plastic experimental instruments. Because of the hydrophobic properties of plastic materials, the surface of a plastic base material is occasionally modified so as to become a hydrophilic surface, so that the base material can be made suitable for applications requiring hydrophilic properties. For example, corona discharge processing, plasma processing, UV ozonation, electron irradiation, or laser processing can be carried out.

PRIOR ART DOCUMENTS

Patent Documents

[Patent Document 1] JP 2005-164348 A
[Patent Document 2] JP 2006-143715 A
[Patent Document 3] JP 2006-509201 A

DISCLOSURE OF THE INVENTION

Objects to be Attained by the Invention

In general, plastic materials are easy to shape, and, advantageously, plastic materials are less problematic in terms of transportation and waste management. Accordingly, plastic materials are preferably used for biochemical test instruments, such as an immunoassay carrier for ELISA. In the past, however, it had been difficult to introduce a PEG linker, which binds a substance to be fixed in immunoassays or a hydrophilic layer comprising ethylene glycol (EG) or PEG that makes the surface of an instrument hydrophilic, onto a site on the surface of a support comprising plastic materials. For example, a conventional immunoassay carrier having a PEG linker was required to use an inorganic material, such as a glass or gold, as a support for the following reasons. That is, it was difficult to introduce a functional group serving as the origin for ligation of a PEG chain to a surface comprising a plastic material, and most plastic materials are less tolerant to chemical agents.

Accordingly, it is an object of the present invention to provide a base material composed of a support containing a plastic material and, on its surface, a hydrophilic layer comprising an ethylene glycol chain composed of one or more ethylene glycol units (hereafter referred to as the "EG chain"), as well as a method for producing such base material.

Means for Attaining the Object

The present inventors discovered that the object mentioned above could be attained by a method comprising providing a polysiloxane-containing primer layer on a support containing a plastic material on its surface, and allowing PEG or EG to covalently bind to a polysiloxane side chain, so as to form an EG chain-containing hydrophilic layer on the primer layer. This has led to the completion of the present invention. The present invention includes the following.

(1) A base material comprising at least:
a support containing a plastic material on its surface;
a polysiloxane-containing primer layer on the surface of the support; and
on the primer layer, a hydrophilic layer containing an ethylene glycol chain composed of one or more ethylene glycol units, which is covalently bound to a side chain of the polysiloxane of the primer layer.

(2) The base material according to (1), wherein the primer layer is bound to the surface of the support by physical adsorption.

(3) The base material according to (2), wherein the plastic material is at least one member selected from the group consisting of polystyrene, polypropylene, polyvinyl chloride, polyethylene, cyclic polyolefin, acrylic resin, and polyethylene terephthalate.

(4) The base material according to any of (1) to (3), wherein one end of the ethylene glycol chain is covalently bound to the side chain of the polysiloxane of the primer layer and the other end of the ethylene glycol chain is bound to a functional group capable of forming a covalent bond with another substance.

(5) The base material according to (4), wherein the functional group comprises a functional group having n number of nitrogen atoms and the nitrogen concentration in the hydrophilic layer is from 0.010 to 0.050×n, provided that the carbon concentration resulting from C—O bonds in the hydrophilic layer is 1.

(6) The base material according to any of (1) to (3), wherein one end of the ethylene glycol chain is covalently bound to the side chain of the polysiloxane of the primer layer and the other end of the ethylene glycol chain is sealed with a hydroxyl group.

(7) A method for producing the base material according to any of (1) to (6) comprising:

a step of forming a primer layer on the surface of the support comprising polymerizing a silanol compound containing an organic group having a carbon atom directly bound to a silicon atom and a functional group, so as to form a polysiloxane-containing primer layer; and a step of forming a hydrophilic layer comprising allowing the primer layer to react with ethylene glycol or polyethylene glycol through a reaction between a hydroxyl group of the ethylene glycol or polyethylene glycol and a functional group on a side chain of the polysiloxane which corresponds to the functional group of the silanol compound or is derived from the functional group of the silanol compound, so as to form a covalent bond between the ethylene glycol chain composed of one or more ethylene glycol units and the side chain.

(8) The method according to (7), wherein the step of forming a primer layer comprises:

a step of hydrolyzing a silicon compound that generates the silanol compound via hydrolysis, so as to generate the silanol compound; and a step of bringing a solution comprising the silanol compound and a base dissolved in an alcohol into contact with the surface of the support.

(9) The method according to (8), wherein the silicon compound is 3-glycidoxypropyltrimethoxysilane or 3-glycidoxypropyltriethoxysilane.

(10) The method according to any of (7) to (9), which further comprises a step of binding a functional group capable of forming a covalent bond with another substance to an end of the ethylene glycol chain that is not bound to the polysiloxane, following the step of forming a hydrophilic layer, wherein the step of binding a functional group comprises a step of bringing a solution comprising a precursor compound that imparts the functional group through the reaction with a hydroxyl group of the ethylene glycol chain dissolved in substantially anhydrous acetonitrile or dimethyl sulfoxide or a solvent mixture thereof into contact with the hydrophilic layer at 4° C. to 25° C.

(11) The method according to (10), wherein the functional group is (1H-imidazol-1-yl)carbonyl group and the precursor compound is 1,1'-carbonyldiimidazole, or the functional group is succinimidyloxycarbonyl group and the precursor compound is di(N-succinimidyl) carbonate.

This description includes part or all of the content as disclosed in the description and/or drawings of Japanese Patent Application No. 2011-143259, which is a priority document of the present application.

Effects of the Invention

According to the present invention, a hydrophilic layer containing an EG chain can be introduced onto the surface of a support containing a plastic material.

BRIEF DESCRIPTION OF THE DRAWINGS

FIG. 14 shows the test results attained in Example 5.

EMBODIMENTS FOR CARRYING OUT THE INVENTION

[The Base Material of the Present Invention]

Figure 7:
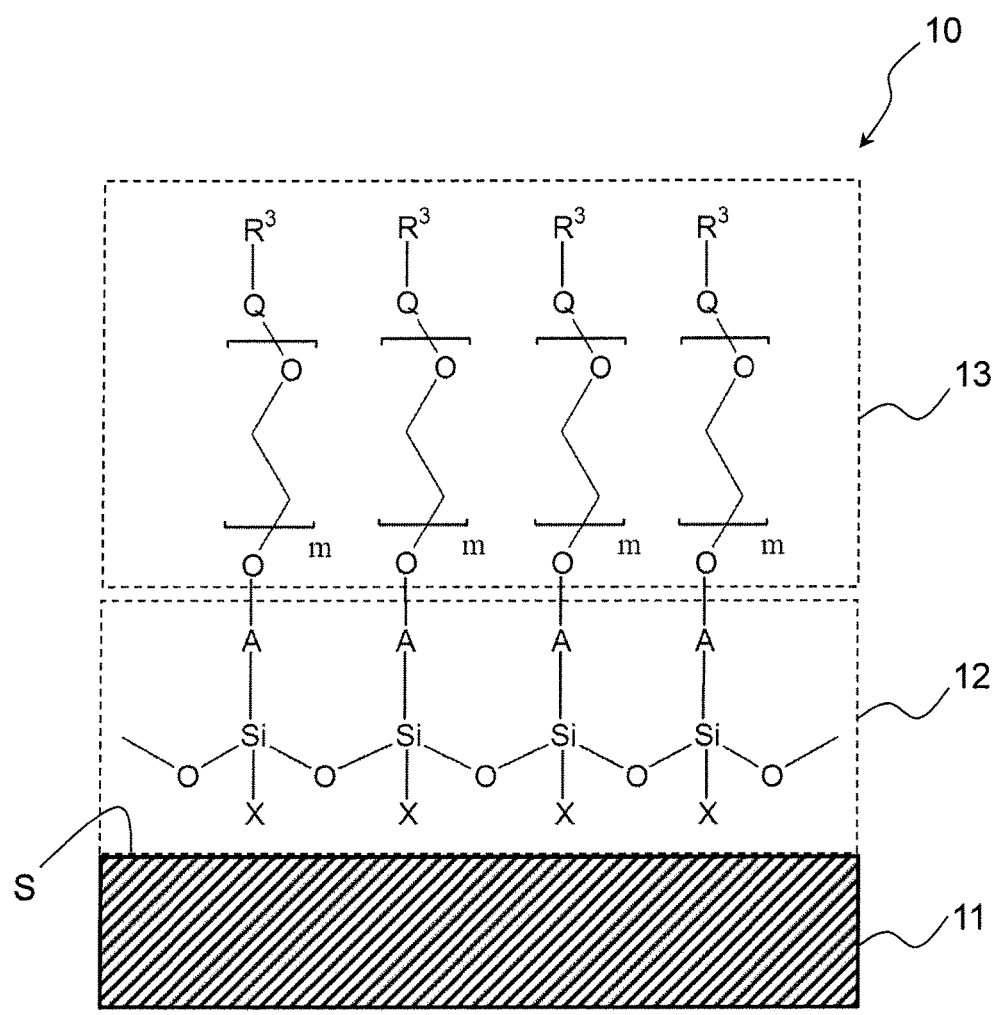
FIG. 7 shows an embodiment of the base material of the present invention.

At the outset, the general constitution of the base material of the present invention is briefly described with reference to FIGS. 7 and 8.

The base materials 10 and 10' each comprise: the support 11 containing a plastic material on a surface S; the polysiloxane-containing primer layer 12 provided on the surface S; and hydrophilic layers 13 and 13' each comprising an ethylene glycol chain (EG chain) provided on the primer layer 12.

The EG chain of the hydrophilic layer 13 is represented by the following formula: —$(CH_2—CH_2—O)_m$—, wherein m is an integer of 1 or larger, and such EG chain is covalently bound to a polysiloxane side chain A constituting the primer layer 12. The side chain A is a group derived from $R^1$ of a silanol compound represented by Formula 1 below, which is a divalent group formed via a covalent bond of a functional group of $R^1$ or a functional group derived therefrom with a hydroxyl group at an end of the EG chain. A group (X) binding to a silicon atom is derived from $R^1$ (when p=2), $R^2$ (when p+q=3), or a hydroxyl group (when q=3) of a silanol compound represented by Formula 1. In the primer layer 12, polysiloxane may have a linear, branched, or network structure, with a branched or network structure being preferable. When polysiloxane has a branched or network structure, X is a crosslinking group that binds to a silicon atom of another repeat unit (not shown). An example of X as a crosslinking group is an ether group (—O—) derived from a hydroxyl group in a silanol compound represented by Formula 1. When polysiloxane has a linear structure, X is a monovalent group, such as $R^1$ or $R^2$ as defined in Formula 1, an unreacted hydroxyl group, or a group Y remaining unhydrolyzed as defined in Formula 2. To an end of the EG chain that is not bound to polysiloxane, a functional group capable of forming a covalent bond with another substance represented by $R^3$ may be bound directly or indirectly via a linker, according to need. Alternatively, an end that is not bound to polysiloxane may be sealed with a hydroxyl group, as shown in FIG. 8. In FIG. 7, Q represents a bond or a linker.

The base material 10 comprising a functional group $R^3$ introduced onto an end of the EG chain can be used as a carrier onto which a substance was fixed for further fixing a substance of interest, such as a solid-phase carrier for immunoassays. The base material 10' comprising the EG chain sealed with a hydroxyl group at its end can be used for a variety of applications as a base material having a hydrophilic surface. For example, the base material 10' can be used as a base material for cell culture without cell adhesion or as a base material for various homogeneous assays (e.g., fluorescence polarization or fluorescence resonance energy transfer assays).

The support 11 comprises a plastic material at least on the surface S. The polysiloxane-containing primer layer 12 can bind to the surface S of the support 11 through physical adsorption. Physical adsorption is considered to take place by means of the Van der Waals force or hydrophobic interaction. Between the primer layer 12 and the surface S of the support 11, formation of a chemical bond such as a covalent bond is not necessary. When the surface S comprises a plastic material containing no reactive functional group, such as polystyrene, accordingly, the primer layer 12 can bind thereto.

Figure 2:
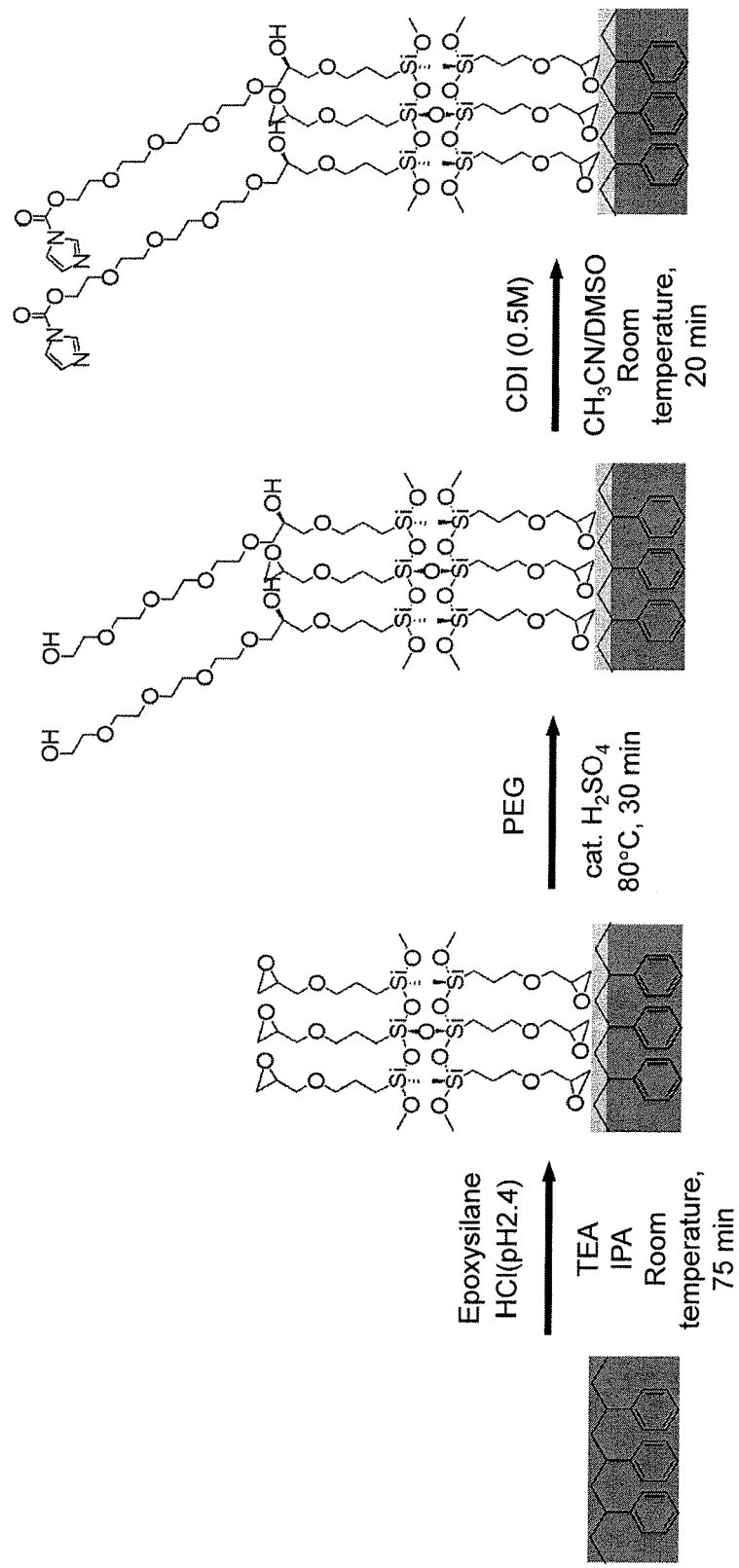
FIG. 2 shows an embodiment of the present invention relating to a method for producing a carrier onto which a substance is to be fixed.

While the condition of polysiloxane in the primer layer 12 is not apparent, as shown in FIG. 2, main chains of a plurality of polysiloxane molecules may aggregate, and organic groups constituting the side chain may form a bilayer structure exposed to the surface of the support and to the hydrophilic layer. The mechanism of formation of such dual structure is deduced to be as follows. At the outset, polysiloxane with an increased Van der Waals force as a result of the polymerization of silanol is physically adsorbed onto the plastic surface. At this time, hydrophobic interactions take place between the plastic surface and organic groups of the silanol compound, and the organic groups of the silanol compound are thus oriented toward the plastic material. After the first polysiloxane layer is formed, another polysiloxane binds to the silanol group (Si—OH) oriented toward the solvent. At this time, hydrogen bonds are formed between silanol groups, and organic groups of the silanol compound are then oriented toward the solvent. It is deduced that polysiloxane has a dual structure as shown in FIG. 2, as a consequence. Organic groups oriented toward the solvent can be covalently bound to the hydrophilic layer.

The base material of the present invention can be used as a carrier onto which a substance is to be fixed or a base material with a hydrophilic surface for various applications, such as a solid-phase carrier for immunoassays, an affinity carrier, a carrier for TAS (Micro-Total Analysis Systems), a biochip carrier, a biosensor carrier, a base material for cell culture, various homogeneous assays, and other purposes.

(Support)

Materials and shape of the support of the present invention are not particularly limited.

A support contains a plastic material at least on the surface on which a primer layer is formed. More preferably, the entire support is composed of a plastic material. Specific examples of plastic materials include polystyrene, polypropylene, polyvinyl chloride, polyethylene, cyclic polyolefin, acrylic resin, and polyethylene terephthalate. The surface of a support may be subjected to physical processing, such as plasma processing or corona discharge processing, in advance. The entire shape of the support is not particularly limited, provided that the support has a surface on which a primer layer can be formed. For example, the support can be in the form of a micro-well plate (a plate on which a plurality of concaves are formed), particle, slide, tube, capillary, or micro-fluid path. A support in the form of a micro-well plate, and, in particular, a polystyrene micro-well plate, is useful for applications in biochemical testing in the form of, for example, a carrier for immunoassays or a base material for cell culture.

(Primer Layer)

A primer layer can be formed in the form of a layer containing at least polysiloxane. Polysiloxane is a polymer comprising repeat units of siloxane bonds (Si—O—Si), which can be obtained by condensation polymerization of silanol compounds. Condensation of silanol compounds is a reaction that takes place among molecules of silanol compounds. When plastic molecules on the support surface do not have reactive functional groups, a reaction does not take place between silanol compounds and plastic molecules on the support surface. Specifically, silanol compounds and the polysiloxane thus obtained do not undergo chemical reactions with plastic molecules on the support surface, and they are merely physically adsorbed thereto. This is significantly different from cases in which a glass support is used. While the physical adsorption force of such silanol compounds to a plastic surface is very weak in the form of a monomer, such force is strengthened when such compound is converted into a polymer (i.e., polysiloxane) as condensation advances to some extent. A polysiloxane-containing primer layer is formed on the plastic surface through adequate condensation of silanol compounds.

Figure 9:
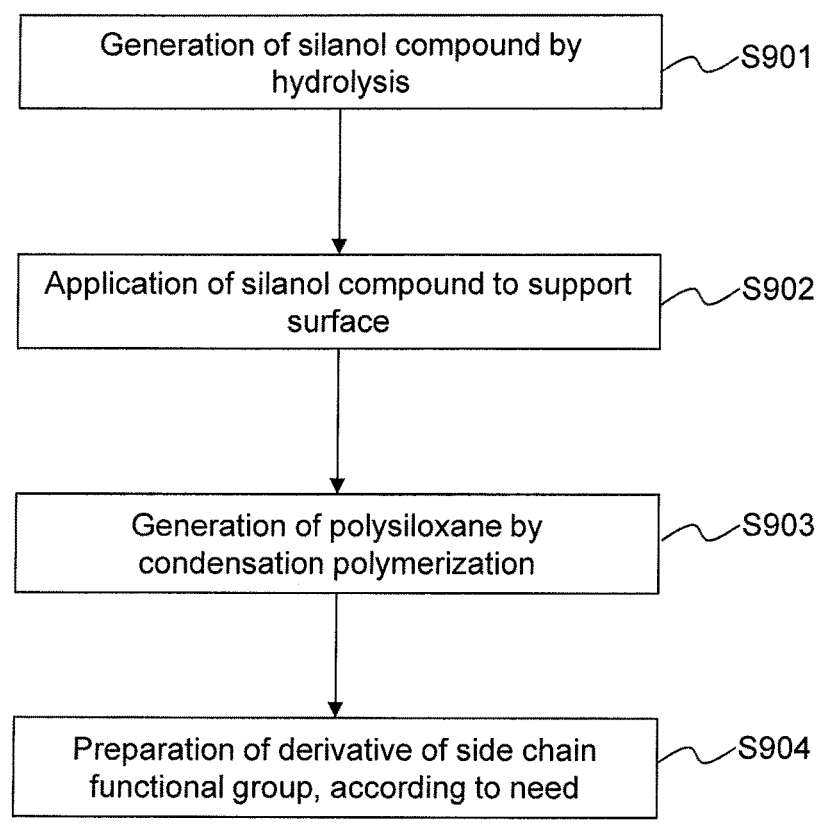
FIG. 9 shows an embodiment of a procedure of the method of forming a primer layer.

FIG. 9 schematically shows a procedure for forming a primer layer on the support surface.

(Silanol Compound)

The silanol compound used in the present invention comprises an organic group containing a carbon atom directly bound to a silicon atom and a functional group, in addition to a silanol group (Si—OH). This organic group serves as a polysiloxane side chain. A typical silanol compound has a structure represented by Formula 1:

(Formula 1)

wherein p is 1 or 2; q is 2 or 3; p+q is 3 or 4; $R^1$ independently represents an organic group containing a carbon atom directly bound to a silicon atom and a functional group; and $R^2$ represents an organic group containing a carbon atom directly bound to a silicon atom. It is preferable that p be 1 and q be 2 or 3, and it is more preferable that p be 1 and q be 3. When the sum of p and q is 4, $R^2$ does not exist.

$R^1$ is preferably a hydrocarbon group having 1 to 20, preferably 1 to 15, more preferably 1 to 10, and particularly preferably 1 to 6 carbon atoms in which a hydrogen atom is substituted with at least 1 (preferably 1) functional group via an adequate linker, according to need. It should be noted that a hydrogen atom is not necessarily substituted with a functional group when the hydrocarbon group itself is a functional group, as in the case in which the entire or part of the hydrocarbon group is a vinyl group. The hydrocarbon group may be a saturated or unsaturated aliphatic hydrocarbon group having a linear, branched, or cyclic structure (i.e., an alkyl group, an alkenyl group having 2 or more carbon atoms, or an alkynyl group having 2 or more carbon atoms). It may be a monocyclic or polycyclic aromatic hydrocarbon group having 6 or more carbon atoms, the aromatic hydrocarbon group substituted with at least one of the aliphatic hydrocarbon groups above, or the aliphatic hydrocarbon group substituted with at least one of the aromatic hydrocarbon groups above. A C—C bond of the hydrocarbon group may be interrupted by 1 atom or 2 of the same or different atoms selected from among oxygen, nitrogen, and sulfur atoms. Preferable examples of hydrocarbon groups are propyl and ethyl groups.

A functional group in $R^1$ that substitutes for at least one hydrogen atom of the hydrocarbon group via an adequate linker, according to need, is not particularly limited, provided that such functional group is capable of reacting with a hydroxyl group of EG or PEG to form a covalent bond therewith or it can be converted into a functional group capable of reacting with a hydroxyl group of EG or PEG to form a covalent bond therewith. Typical examples include a (1H-imidazol-1-yl)carbonyl group, a succinimidyloxycarbonyl group, a glycidyl group, an epoxy group, an aldehyde group, an amino group, a thiol group, a carboxyl group, an azide group, a cyano group, an active ester group (e.g., a 1H-benzotriazol-1-yloxycarbonyl group, a pentafluorophenyloxycarbonyl group, or a paranitrophenyloxycarbonyl group), a halogenated carbonyl group, an isocyanate group, and a maleimide group, with the glycidyl or epoxy group being particularly preferable. While the glycidyl or epoxy group itself is capable of reacting with the hydroxyl group of EG or PEG and forming a covalent bond therewith, the glycidyl or epoxy group may be converted into an aldehyde group, and the resulting aldehyde group may be allowed to react with the hydroxyl group of EG or PEG, in accordance with the method described in JP 2009-156864 A. Such functional groups may directly substitute for the hydrogen atom of the hydrocarbon group or indirectly substitute for via an adequate linker. An example of a linker structure is a divalent group having 0 to 3 carbon atoms and 0 to 3 identical or different hetero atoms selected from among nitrogen, oxygen, and sulfur atoms. When a hydrocarbon group is bound thereto on the left side and a functional group is bound thereto on the right side, for example, such structure can be represented as follows: —O—, —S—, —NH—, —(C=O)O—, —O(C=O)—, —NH(C=O)—, —(C=O)NH—, —(C=O)S—, —S(C=O)—, —NH(C=S)—, —(C=S)NH—, —(N=C=N)—, —CH=N—, —N=CH—, —O—O—, —S—S—, or —(O=S=O)—.

According to a particularly preferable embodiment, $R^1$ is, for example, a 3-glycidoxypropyl group or a 2-(3,4-epoxycyclohexyl)ethyl group.

$R^2$ is preferably a hydrocarbon group as defined with reference to $R^1$, except that it is not substituted with a substituent ($R^2$ is selected independently from $R^1$). A linear or branched alkyl group having 1 to 6 carbon atoms is more preferable, with a methyl or ethyl group being particularly preferable.

(Silicon Compound that Generates Silanol Compound Via Hydrolysis)

The silanol compound can be obtained by hydrolyzing a silicon compound having a group capable of generating a silanol group (Si—OH) via hydrolysis. Such silicon compound has a structure represented by Formula 2:

$$(R^1)_p(R^2)_{4-p-q}Si(Y)_q \qquad \text{(Formula 2)}$$

wherein Y independently represents a group capable of generating a silanol group via hydrolysis; and p, q, $R^1$, and $R^2$ are as defined with reference to the silanol compound.

Preferable examples of groups represented by Y include an alkoxy group, a halogen atom, an aryloxy group, an alkoxy group substituted with an alkoxy group or an aryloxy group, an aryloxy group substituted with an alkoxy group or an aryloxy group, and an alkylcarbonyloxy group. Particularly preferably, Y is an alkoxy group having 1 to 6 carbon atoms (a methoxy, ethoxy, isopropoxy, or tert-butoxy group, in particular), an alkoxy group having 1 to 6 carbon atoms substituted with an alkoxy group (e.g., a methoxyethoxy group), an alkylcarbonyloxy group having 1 to 6 carbon atoms (e.g., an acetoxy group), or a chlorine atom.

A compound commercialized as a silane coupling agent can be preferably used as the silicon compound represented by Formula 2, and 3-glycidoxypropyltrimethoxysilane or 3-glycidoxypropyltriethoxysilane is particularly preferable.

(Method for Forming Primer Layer)

When a primer layer is formed, the silicon compound represented by Formula 2 is subjected to hydrolysis in the manner described below, so that the silanol compound represented by Formula 1 can be generated (S901). While hydrolysis conditions are not particularly limited, hydrolysis can be carried out in the manner described below, for example. At the outset, diluted hydrochloric acid is added to the silicon compound represented by Formula 2, so as to hydrolyze a group Y. It is preferable that the pH level of diluted hydrochloric acid be adjusted to 2.0 to 3.0. The molar ratio of water molecules to the silicon compound is 2 to 4. Thus, the group Y is converted into a silanol group, and the silanol compound represented by Formula 1 is generated.

Subsequently, the silanol compound is applied to the support surface (S902) to generate polysiloxane via condensation polymerization (S903). The silanol compound represented by Formula 1 is dissolved in alcohol with bases. It is preferable that the final concentration of the silanol compound be adjusted to 0.1% to 10% (v/v). Examples of bases that can be used include, but are not limited to, triethylamine, N,N-diisopropylethylamine, pyridine, and 4-dimethylaminopyridine. It is preferable that the final concentration of the bases be adjusted to 0.1% to 10% (v/v). Examples of alcohols that can be used include, but are not limited to, ethanol, 2-propanol, and tert-butyl alcohol. The solution of the silanol compound is brought into contact with the plastic surface of the support, and the support is allowed to stand for 10 minutes to 24 hours. The reaction temperature can be adjusted to 4° C. to 80° C., with room temperature (20° C. to 25° C.) being particularly preferable. Thus, a polysiloxane-containing primer layer is formed on the plastic surface via physical adsorption. The coating density of the primer layer can be regulated in accordance with the silanol or base concentration, the duration during which the silanol solution is in contact with the plastic surface, or other conditions. As the primer layer-coating density is increased, the binding density of the EG chain to be subjected to covalent binding in the subsequent step is increased.

When a functional group of the polysiloxane side chain from a silanol compound is converted into another functional group, following the step of forming a primer layer, a step of derivative preparation for converting a functional group of the polysiloxane side chain from a silanol compound into a functional group capable of reacting with a hydroxyl group of EG or PEG and forming a covalent bond therewith is carried out (S904).

(Hydrophilic Layer)

A hydrophilic layer provided on the primer layer comprises at least an ethylene glycol chain (EG chain) composed of one or more ethylene glycol units ($CH_2$—$CH_2$—O). The term "ethylene glycol chain (or EG chain)" refers to a structure represented by the following formula:

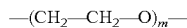

—($CH_2$—$CH_2$—O)$_m$— wherein m is an integer representing the polymerization degree. In the present description, an EG chain exhibiting a polymerization degree (m) of 2 or higher is occasionally referred to as the "polyethylene glycol chain (or PEG chain)."

The molecular weight of the EG chain is not particularly limited, and it can be adequately determined in accordance with the application of the base material. When the base material of the present invention is used as a carrier onto which a substance is to be fixed for immunoassays, preferably, the number average molecular weight of the EG chain is 44 or higher when "m" is 1 or higher, and it is 176 or higher when "m" is 4 or higher. The upper limit of the number average molecular weight of the EG chain is not particularly limited. As the number average molecular weight is increased, the viscosity is increased, and handling becomes more difficult. In addition, it is difficult to provide an EG chain at a high density. Accordingly, the number average molecular weight of the EG chain is preferably 25,000 or lower, and more preferably 10,000 or lower.

The EG chain can be formed using ethylene glycol (EG; m is 1) or polyethylene glycol (PEG; m is 2 or higher) represented by the following formula:

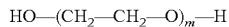

HO—($CH_2$—$CH_2$—O)$_m$—H wherein m is an integer representing the polymerization degree.

The number average molecular weight of the EG chain can be determined by subtracting the molecular weight of $H_2O$ (18.015) from the number average molecular weight of EG or PEG used as a raw material or EG or PEG dissociated from the carrier. The number average molecular weight of EG or PEG can be determined using a vapor pressure osmometer or membrane osmometer. A vapor pressure osmometer can be used when the number average molecular weight of EG or PEG is less than 100,000. A membrane osmometer can be used when the number average molecular weight of PEG is 10,000 to 1,000,000.

The EG chain is bound to the primer layer through a covalent bond formed via a reaction between a hydroxyl group at one end of EG or PEG and the functional group of the polysiloxane side chain or a functional group derived therefrom.

Figure 8:
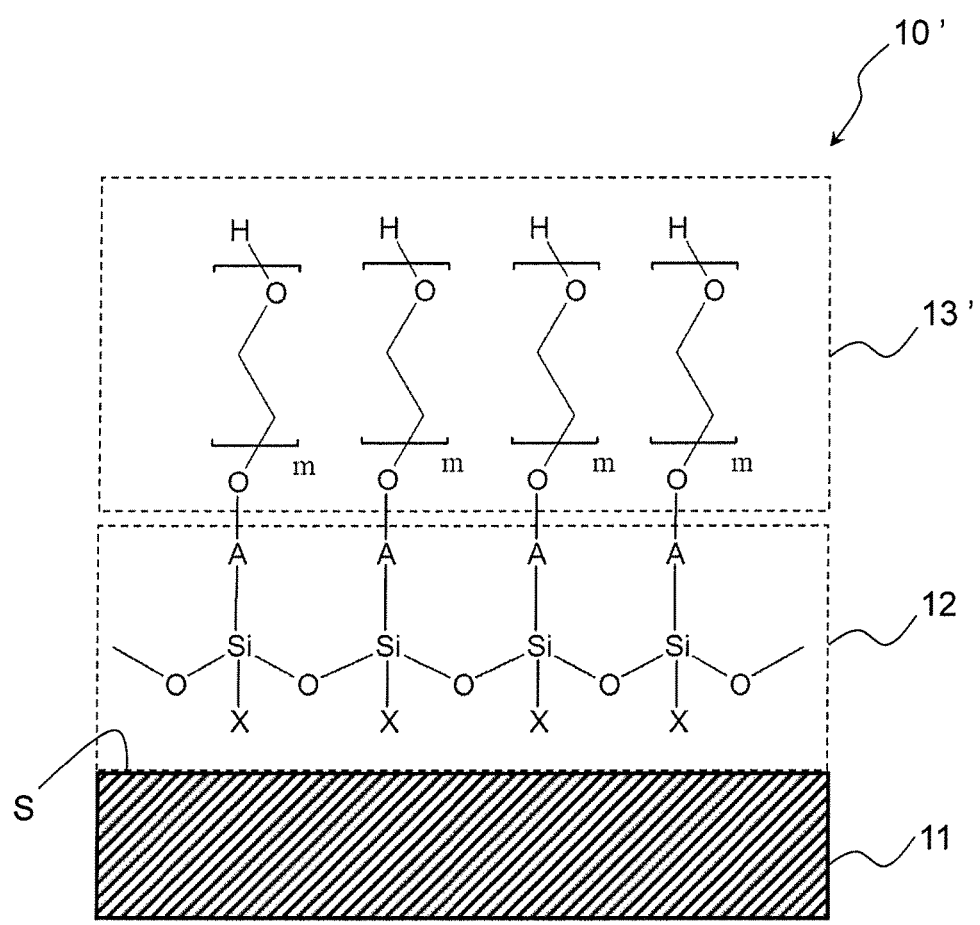
FIG. 8 shows an embodiment of the base material of the present invention.

The other end of the EG chain may be sealed with a hydroxyl group, which does not form a derivative, as shown in FIG. 8. Alternatively, at least one functional group represented by $R^3$, which is capable of forming a covalent bond with another substance, may be directly (Q represents a bond) or indirectly (Q represents a linker) bound thereto, as shown in FIG. 7.

The functional group to be introduced onto the other end of the EG chain represented by $R^3$ is not particularly limited, provided that such functional group is capable of forming a covalent bond with another substance. Typical examples of functional groups include a (1H-imidazol-1-yl)carbonyl group, a succinimidyloxycarbonyl group, an epoxy group, an aldehyde group, an amino group, a thiol group, a carboxyl group, an azide group, a cyano group, an active ester group (e.g., a 1H-benzotriazol-1-yloxycarbonyl group, a pentafluorophenyloxycarbonyl group, or a paranitrophenyloxycarbonyl group), and a halogenated carbonyl group (e.g., a carbonyl chloride group, a carbonyl fluoride group, a carbonyl bromide group, or a carbonyl iodide group). Such a functional group may be directly bound to the EG chain as a substituent that substitutes for the hydrogen atom of the hydroxyl group at the end of the EG chain. Alternatively, a functional group may be indirectly bound to the EG chain via a linker structure bound to the end of the EG chain. From the viewpoint of the balance between reactivity with other substances and storage stability, the (1H-imidazol-1-yl)carbonyl group and the succinimidyloxycarbonyl group are preferable. Such functional groups can react with other functional groups, such as an amino group of another substance, so as to form a covalent bond therewith. An example of a linker structure is a divalent group having 0 to 3 carbon atoms and 0 to 3 identical or different hetero atoms selected from among the nitrogen, oxygen, and sulfur atoms.

According to the present invention, the EG chain-binding density can be regulated by regulating the primer layer-coating density. The EG chain-binding density also affects the detection sensitivity of immunoassays. The EG chain-binding density can be predicted with a certain level of accuracy via X-ray photoelectron spectroscopy (XPS). When XPS is performed, the ethylene glycol unit ($CH_2$—$CH_2$—O) gives C(1 s) signal of the C—O component, and the nitrogen atom-containing functional group, such as a (1H-imidazol-1-yl)carbonyl group or a succinimidyloxycarbonyl group gives N(1 s) signal. The ratio of element concentration (N(1 s)/C—O) is apparently correlated with the EG chain-binding density. In order to carry out immunoassays with high detection sensitivity, the ratio of element concentration N(1 s)/C—O is preferably 0.010 to 0.050×n, when the functional group has n number of nitrogen atoms. The expression "0.010 to 0.050×n" means, for example, "0.010 to 0.050" when n is 1, "0.010 to 0.100" when n is 2, "0.010 to 0.150" when n is 3, and "0.010 to 0.200" when n is 4. In the present invention, XPS is carried out using an X-ray photoelectron spectroscopy (ESCA 5600, ULVAC-PHI, Inc.) at an angle of incidence of photoelectrons of 45 degrees. Examples of functional groups containing n number of nitrogen atoms include an isocyanate group (n=1), an azidocarbonyl group (n=3), a carbodiimide group (n=2), a maleimidyl group (n=1), an aziridin-2-yl group (n=1), a 1H-benzotriazol-1-yloxycarbonyl group (n=3), and a 1H-7-azabenzotriazol-1-yloxycarbonyl group (n=4), in addition to the (1H-imidazol-1-yl)carbonyl group (n=2) and the succinimidyloxycarbonyl group (n=1). Concerning such functional groups, it is preferable that the nitrogen concentration determined via XPS (i.e., N(1 s)/C—O) relative to the carbon concentration resulting from the C—O bond of the hydrophilic layer designated as 1 be in the same numerical range as described above.

A hydrophilic layer may further contain other hydrophilic compounds.

(Method of Forming Hydrophilic Layer)

Figure 10:
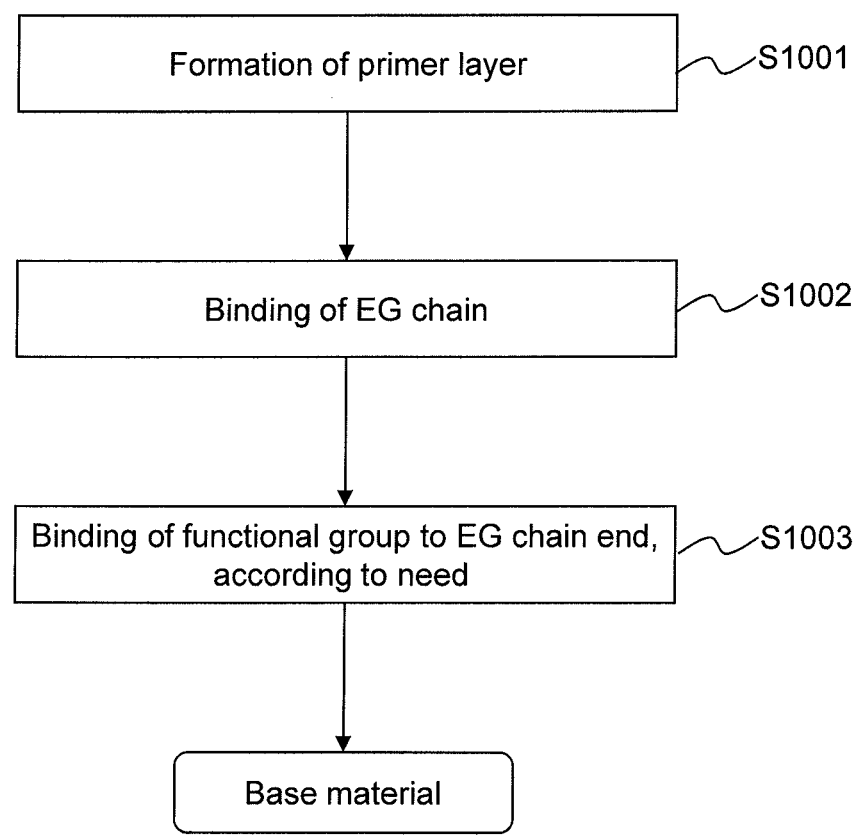
FIG. 10 shows an embodiment of a procedure of the method of forming a base material of the present invention.

The base material of the present invention can be produced by a method comprising at least a step of forming a primer layer (S1001) and a step of binding an EG chain to polysiloxane of the primer layer (S1002), as schematically shown in FIG. 10. When a functional group is to be introduced onto an end of the EG chain as shown in FIG. 7, the method further comprises a step of binding a functional group to an end of the EG chain (S1003).

A hydrophilic layer can be formed through a reaction between a functional group of a polysiloxane side chain of the primer layer (i.e., a functional group corresponding to the functional group of the silanol compound or a functional group derived therefrom) and a hydroxyl group of EG or PEG. At this time, EG or PEG containing a catalytic amount of concentrated sulfuric acid is brought into contact with the primer layer. PEG having a number average molecular weight exceeding 1,000 is heat-melted in advance. According to need, EG or PEG may be diluted with, for example, tert-butyl alcohol. The EG or PEG solution is brought into contact with a plastic surface and heated. The heating temperature can be adjusted to 60° C. to 100° C., with a heating temperature of around 80° C. (e.g., 75° C. to 85° C.) being preferable from the viewpoint of heat resistance of plastics. The heating duration can be set to be between 10 minutes and 24 hours. When the heating temperature is around 80° C., the heating duration is preferably 10 minutes to 60 minutes. Thus, the EG chain is covalently bound to the primer layer. The EG chain-binding density depends on the primer layer-coating density.

According to need, at least 1 functional group that is capable of forming a covalent bond with another substance is directly or indirectly bound to an end of the EG chain. A method of introducing a functional group is not particularly limited. According to a preferable embodiment, the (1H-imidazol-1-yl)carbonyl group and the succinimidyloxycarbonyl group are introduced as substituents that substitute for the hydrogen atoms of the hydroxyl groups at an end of the EG chain in the manner described below. That is, 1,1'-carbonyldiimidazole (hereafter referred to as "CDI") or di(N-succinimidyl) carbonate (hereafter referred to as "DSC") is bound to an end of the EG chain fixed onto the surface of the support via a primer layer, a silane coupling agent, or another agent, as shown in the following formulae:

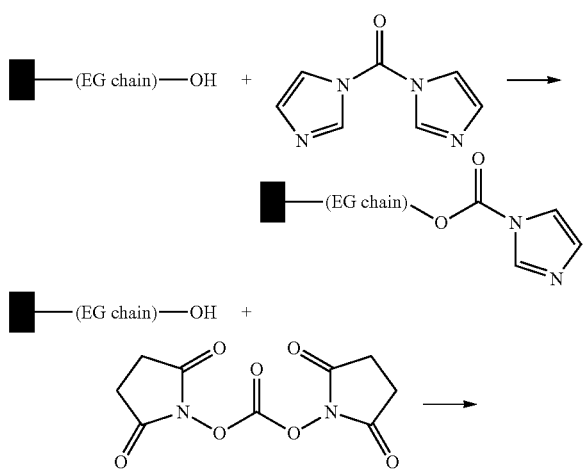

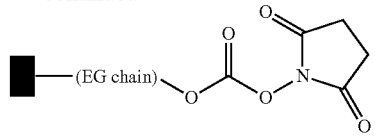

It is necessary to perform the above reaction in a substantially anhydrous organic solvent, which is substantially free of water. In general, plastic materials are less tolerant to organic solvents. When a support contains a plastic material, accordingly, acetonitrile, dimethyl sulfoxide, or a solvent mixture containing such organic solvents at adequate concentrations is preferably used. The moisture content of such organic solvent is preferably 0.1% by weight or lower. The final concentration of CDI or DSC can be adjusted to 0.01 to 1 M, and it is preferably 0.1 M or higher when the reaction is allowed to proceed at room temperature or a lower temperature. It is preferable that the reaction temperature be adjusted to 4° C. to 25° C., in order to prevent the plastic on the support surface from being damaged. The reaction duration is preferably between 10 minutes and 24 hours, and it is preferably between 10 minutes and 60 minutes when the CDI concentration is around 0.5 M (i.e., 0.4 to 0.6 M). Thus, a hydrophilic layer comprising an EG chain to which a functional group is covalently bound can be formed.

(Other Substances)

According to an embodiment of the base material of the present invention, a functional group that has been introduced onto an end of the EG chain may be used to fix "another substance" to the end of the EG chain. According to this embodiment, specifically, the base material of the present invention serves as a carrier onto which a substance is to be fixed, and the "other substance" is a substance to be fixed. Hereafter, the "other substance" is occasionally referred to as a "substance to be fixed."

A substance to be fixed is not particularly limited, provided that it has a functional group capable of forming a covalent bond with a functional group that has been introduced onto an end of the EG chain. A representative example of such functional group is an amino group, and such functional group may be a thiol group, a carboxyl group, a hydroxyl group, an azide group, or a cyano group. Other examples of substances to be fixed include alkoxide, secondary amine, tertiary amine, a Grignard reagent, an organic lithium compound, and carbanion. A substance to be fixed is preferably a biologically relevant substance. Examples of biologically relevant substances include DNAs, RNAs, peptides, hormones, enzymes, antigens, antibodies cytokines, sugar chains, lipids, coenzymes, enzyme inhibitors, cells, and other functional proteins. In addition, low-molecular-weight compounds and high-polymer-weight compounds having affinity with such biologically relevant substances are within the scope of biologically relevant substances. When a biologically relevant substance to be fixed does not have a functional group capable of forming a covalent bond with a functional group that has been introduced onto an end of the EG chain (e.g., an amino group), an amino group or another group may be artificially introduced into such substance, so as to fix the substance.

When the base material of the present invention is used as a solid-phase carrier for immunoassays, an antigen or antibody that binds to a target substance or a target substance is fixed thereto in accordance with the forms of immunoassays of interest. According to an embodiment in which "an antigen or antibody that binds to a target substance" is a substance to be fixed (i.e., the sandwich assay technique or direct competitive assay technique), a combination of a substance to be fixed with a target substance is not particularly limited, provided that specific antigen-antibody binding can be performed. When a target substance is an antigen (including hapten), for example, the substance to be fixed can be an antibody (including an antibody fragment). When the target substance is an antibody (including an antibody fragment), for example, the substance to be fixed can be an antigen (including hapten). According to an embodiment in which a "target substance" is a substance to be fixed (i.e., the indirect competitive assay technique), the target substance is an antigen (including hapten) or an antibody (including an antibody fragment).

An antigen as a substance to be fixed and/or target substance is not particularly limited, provided that it can show specific antigen-antibody reactivity to an antibody. Examples of representative antigens include naturally occurring antigens, such as proteins, peptides, saccharides, nucleic acids (DNA and RNA), lipids, coenzymes, cells, viruses, bacteria, composites of any thereof, derivatives of naturally occurring antigens, artificially synthesized hapten, and artificial antigens.

An antibody as a substance to be fixed and/or target substance is an immunoglobulin or a fragment thereof showing specific antigen-antibody reactivity to a certain type of antigen. According to need, such antibody may be chemically modified.

Immunoassays can be performed by assaying a target substance using a carrier onto which a substance was fixed comprising, at an end of the EG chain of the base material of the present invention, an antigen or antibody that binds to a target substance or a target substance fixed thereonto. Immunoassays involving the use of the base material of the present invention can be performed in accordance with conventional techniques, such as sandwich, direct competitive, or indirect competitive techniques.

A means of detecting an antigen or antibody in immunoassays involving the use of the base material of the present invention is not particularly limited. An antigen or antibody directly or indirectly labeled with any label can be used. Examples of labels include those capable of generating amplified detection signals, such as enzymes (ELISA), nucleic acids (immuno-PCR), electrochemical luminescent substances (electrochemical luminescence assays), fluorescent substances, chemical luminescent substances, and radioactive substances. The immunoassay technique is preferably an enzyme-linked immunosorbent assay (ELISA) that performs detection based on the enzyme activity with the use of an enzyme label, from the viewpoint of safety and convenience.

Hereafter, the present invention is described with reference to the figures and the examples.

Example 1

Figure 1:
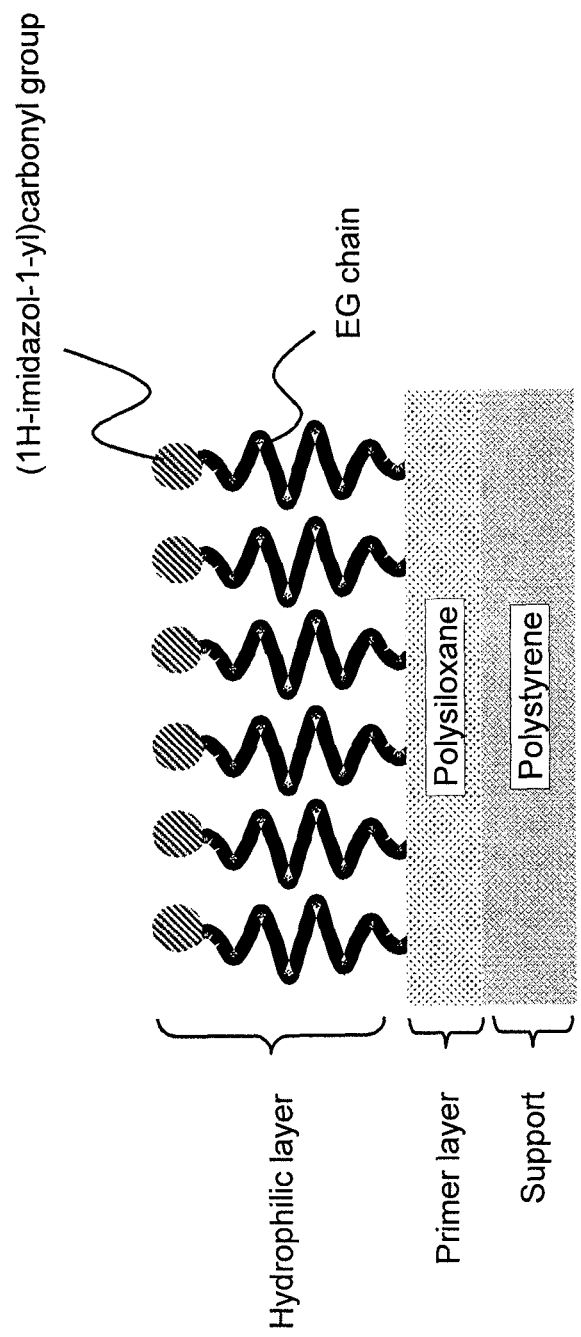
FIG. 1 shows an embodiment of the present invention relating to a carrier onto which a substance is to be fixed.

FIG. 1 shows an embodiment of the base material of the present invention (a carrier onto which a substance is to be fixed). A polysiloxane-containing primer layer is provided on the surface of the polystyrene support. An end of the EG chain is covalently bound to the primer layer. (1H-imidazol-1-yl)carbonyl is present on the other end of the EG chain.

Example 2

A carrier onto which a substance is to be fixed was produced by the method shown in FIG. 2. A specific procedure is described below.

Diluted hydrochloric acid (0.35 ml, pH 2.4) was added to 1.65 ml of 3-glycidoxypropyltrimethoxysilane (Momentive Performance Materials Inc.) to prepare silanol. The resultant was added to 100 ml of 2-propanol (Junsei Chemical Co., Ltd.). Further, 4 ml of triethylamine (Wako Pure Chemical Industries, Ltd.) was added thereto. The silanol solution was applied to a 96-well microplate (BD Falcon™) in an amount of 100 µl/well. The plate was allowed to stand in such state at room temperature for 75 minutes. Thereafter, the insides of the wells were washed with pure water and dried by nitrogen blowing. Thus, a primer layer comprising polysiloxane and epoxy groups was formed in the wells of the microplate. Subsequently, PEG 4000 containing a catalytic amount of concentrated sulfuric acid (the number average molecular weight: 2,700 to 3,400; Kanto Chemical Co., Inc.) was applied to the plate in an amount of 100 µl/well. The plate was heated in such state at 90° C. for 30 minutes. Thereafter, the insides of the wells were washed with pure water and dried by nitrogen blowing. Thus, a hydrophilic layer comprising PEG was formed on the primer layer. Subsequently, a solvent mixture containing equal weights of anhydrous acetonitrile (Kanto Chemical Co., Inc.) and anhydrous dimethyl sulfoxide (Kanto Chemical Co., Inc.) was used to prepare a solution of CDI (final concentration: 0.5 M; Tokyo Chemical Industry Co., Ltd.), the solution was applied to the plate in an amount of 10 µl/well, and the plate was allowed to stand in such state at room temperature for 20 minutes. Thereafter, the insides of the wells were washed with pure water and dried by nitrogen blowing. Thus, a PEG derivative comprising the (1H-imidazol-1-yl)carbonyl group introduced at an end of PEG of the hydrophilic layer was formed.

Example 3

Figure 3:
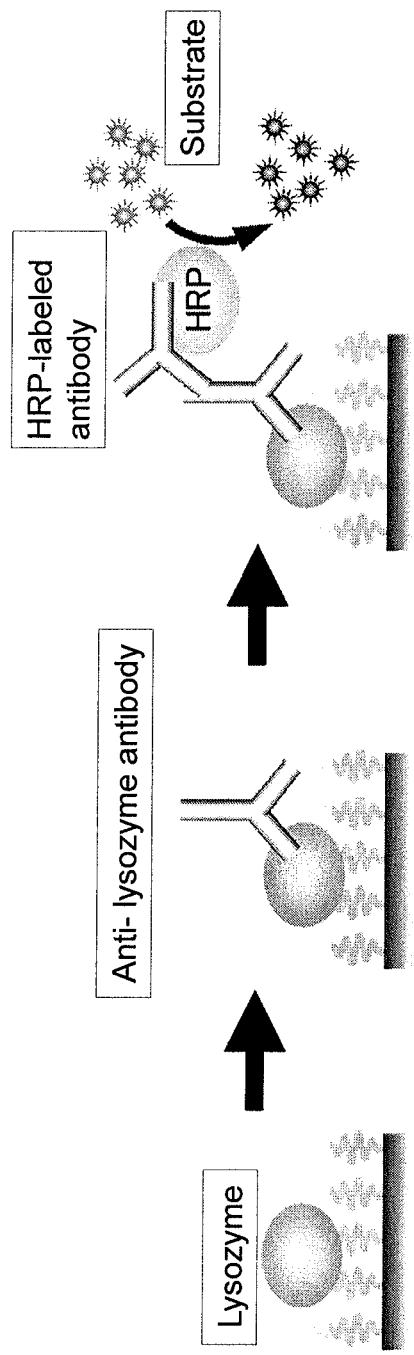
FIG. 3 shows an embodiment of indirect ELISA using the carrier onto which a substance was fixed of the present invention.

ELISAs (the indirect assay and the antigen-antibody-antibody sandwich assay techniques) shown in FIG. 3 were carried out using the carrier onto which a substance is to be fixed (a 96-well microplate) prepared in Example 2. A specific procedure is described below.

Figure 4:
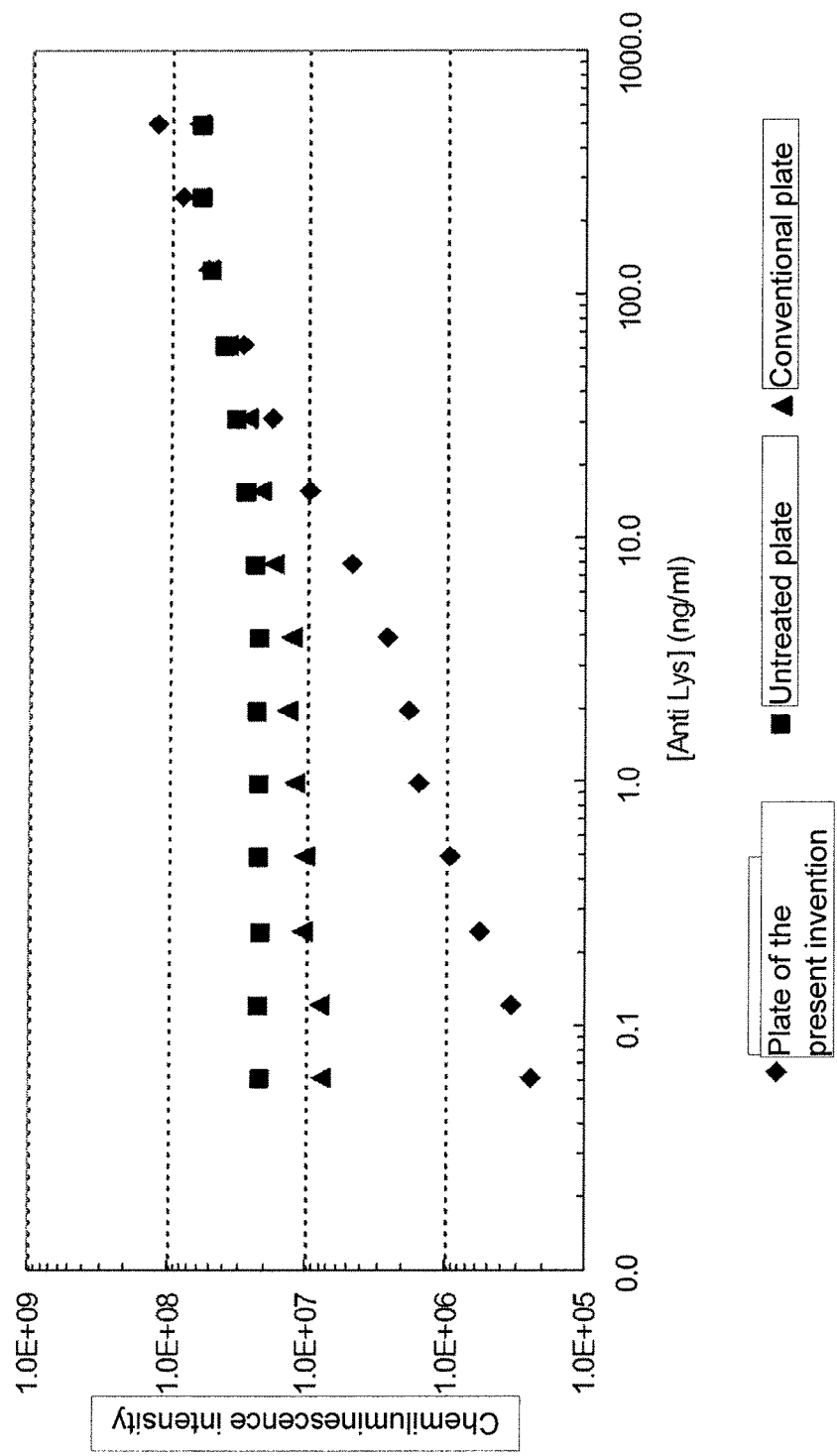
FIG. 4 shows a calibration curve attained by indirect ELISA using the carrier onto which a substance was fixed of the present invention.

Hereafter, a carbonate-bicarbonate buffer (pH 9.6) containing 0.025% Triton® X-100 (Wako Pure Chemical Industries, Ltd.) was used as a fixation buffer, a phosphate buffer (PBS) containing 0.1% Triton® X-100 and 0.5 M NaCl was used as a wash buffer, and PBS containing 1% BSA was used as a dilution buffer. At the outset, lysozyme (Wako Pure Chemical Industries, Ltd.) was dissolved in a fixation buffer to prepare a lysozyme solution (final concentration: 50 µg/ml). The solution was applied to the 96-well microplate prepared in Example 2 in an amount of 5 µl/well. The plate was allowed to stand at 37° C. for 10 minutes to concentrate the solution to dryness, and the insides of the wells were washed twice with a wash buffer. Subsequently, solutions containing anti-lysozyme antibodies (Nordic Immunological Laboratories) at 0 to 500 ng/ml were prepared using a dilution buffer, and the solutions were applied to the plate in an amount of 50 µl/well. After the plate was allowed to stand at room temperature for 30 minutes, the insides of the wells were washed once with a wash buffer. The HRP-labeled secondary antibody (Rockland) was diluted 4,000-fold (final concentration: 0.5 µg/ml) using a dilution buffer, and the resultant was applied to the plate in an amount of 50 µl/well. After the plate was allowed to stand at room temperature for 30 minutes, the insides of the wells were washed three times with a wash buffer. A chemiluminescent substrate (ImmunoStar LD, Wako Pure Chemical Industries, Ltd.) was applied to the plate in an amount of 30 µl/well, and a chemiluminescence image was obtained using an LAS 4000 mini (GE Health Care). In the end, the chemiluminescence intensity was determined using dedicated software, and the calibration curve as shown in FIG. 4 was prepared (the present invention). The sensitivity was 0.03 ng/ml.

Comparative Example 1

With the use of an untreated 96-well microplate (BD Falcon™) and a conventional 96-well microplate (a polystyrene 96-well microplate hydrophilized by enzyme plasma treatment), ELISA (the indirect assay technique) shown in FIG. 3 was performed. A specific procedure is described below.

Hereafter, a carbonate-bicarbonate buffer (pH 9.6) was used as a fixation buffer, PBS containing 0.05% Tween® 20 was used as a wash buffer, and PBS containing 1% BSA was used as a block buffer and as a dilution buffer. At the outset, lysozyme (Wako Pure Chemical Industries, Ltd.) was dissolved in a fixation buffer to prepare a lysozyme solution (final concentration: 5 μg/ml). The solution was applied to the 96-well microplate in an amount of 100 μl/well. The plate was allowed to stand at room temperature for 2 hours, and the insides of the wells were washed twice with a wash buffer. Subsequently, the block buffer was applied to the plate in an amount of 200 μl/well. After the plate was allowed to stand at room temperature for 60 minutes, the insides of the wells were washed twice with a wash buffer. Subsequently, solutions containing anti-lysozyme antibodies (Nordic Immunological Laboratories) at 0 to 500 ng/ml were prepared using a dilution buffer, and the solutions were applied to the plate in an amount of 100 μl/well. After the plate was allowed to stand at room temperature for 60 minutes, the insides of the wells were washed once with a wash buffer. The HRP-labeled secondary antibody (Rockland) was diluted 4,000-fold (final concentration: 0.5 μg/ml) using a dilution buffer, and the resultant was applied to the plate in an amount of 100 μl/well. After the plate was allowed to stand at room temperature for 30 minutes, the insides of the wells were washed three times with a wash buffer. A chemiluminescent substrate (ImmunoStar LD, Wako Pure Chemical Industries, Ltd.) was applied to the plate in an amount of 30 μl/well, and a chemiluminescence image was obtained using an LAS 4000 mini (GE Health Care). In the end, the chemiluminescence intensity was determined using dedicated software, and the calibration curves as shown in FIG. 4 were prepared (the untreated plate and the conventional plate). The sensitivity of the untreated plate and that of the conventional plate were both 3.9 ng/ml.

Example 4

Figure 5:
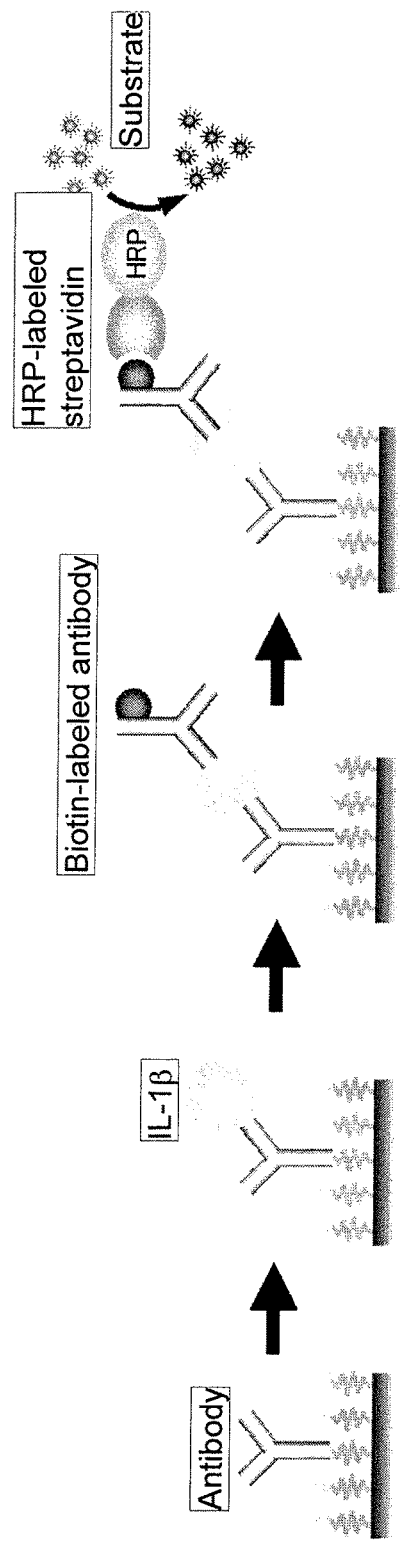
FIG. 5 shows an embodiment of sandwich ELISA using the carrier onto which a substance was fixed of the present invention.

With the use of the 96-well microplate prepared in Example 2, ELISA (the antibody-antigen-antibody sandwich assay) shown in FIG. 5 was performed. A specific procedure is described below.

Figure 6:
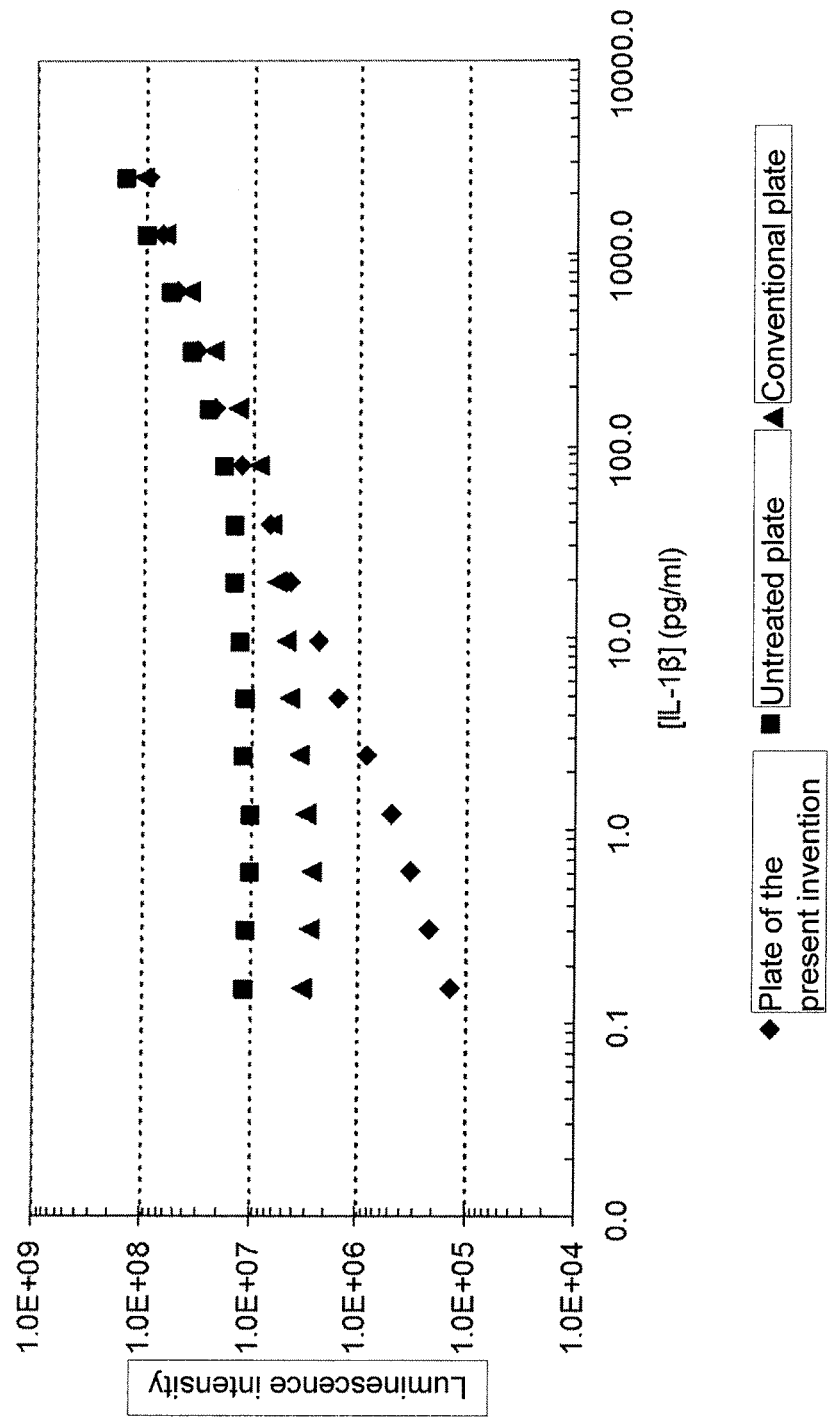
FIG. 6 shows a calibration curve attained by sandwich ELISA using the carrier onto which a substance was fixed of the present invention.

A carbonate-bicarbonate buffer (pH 9.6) containing 5% trehalose (Wako Pure Chemical Industries, Ltd.) and 0.025% Triton® X-100 (Wako Pure Chemical Industries, Ltd.) was used as a fixation buffer. The anti-IL-1β antibody (Biolegend) was dissolved in a fixation buffer to prepare an antibody solution (final concentration: 50 μg/ml). The solution was applied to the 96-well microplate prepared in Example 2 in an amount of 5 μl/well. The plate was allowed to stand at 37° C. for 2 hours to concentrate the solution to dryness, and the insides of the wells were washed twice with a wash buffer. Subsequently, solutions containing 0 to 2,500 pg/ml IL-1β (Wako Pure Chemical Industries, Ltd.) were prepared using a dilution buffer, and the solutions were applied to the plate in an amount of 50 μl/well. After the plate was allowed to stand at room temperature for 60 minutes, the insides of the wells were washed once with a wash buffer. The biotin-labeled secondary antibody (Biolegend) was diluted 500-fold using a dilution buffer, and the resultant was applied to the plate in an amount of 50 μl/well. After the plate was allowed to stand at room temperature for 30 minutes, the insides of the wells were washed once with a wash buffer. Subsequently, HRP-labeled streptavidin (Prozyme) was diluted 4,000-fold (final concentration: 0.25 μg/ml) using a dilution buffer, and the resultant was applied to the plate in an amount of 50 μl/well. After the plate was allowed to stand at room temperature for 10 minutes, the insides of the wells were washed three times with a wash buffer. A chemiluminescent substrate (ImmunoStar LD, Wako Pure Chemical Industries, Ltd.) was applied to the plate in an amount of 30 μl/well, and a chemiluminescence image was obtained using an LAS 4000 mini (GE Health Care). In the end, the chemiluminescence intensity was determined using dedicated software, and the calibration curve as shown in FIG. 6 was prepared (the present invention). The sensitivity was 0.15 pg/ml.

Comparative Example 2

With the use of an untreated 96-well microplate (BD Falcon™) and a conventional 96-well microplate (a polystyrene 96-well microplate hydrophilized by enzyme plasma treatment), ELISA (the antibody-antigen-antibody sandwich assay technique) shown in FIG. 5 was performed. A specific procedure is described below.

Various types of buffers as used in Comparative Example 1 were used. The anti-IL-1β antibody (Biolegend) was dissolved in a fixation buffer to prepare an antibody solution (final concentration: 5 μg/ml). The solution was applied to the 96-well microplate in an amount of 50 μl/well. The plate was allowed to stand at room temperature for 2 hours, and the insides of the wells were washed twice with a wash buffer. Subsequently, a block buffer was applied to the plate in an amount of 100 μl/well. After the plate was allowed to stand at room temperature for 60 minutes, the insides of the wells were washed twice with a wash buffer. Subsequently, solutions containing 0 to 2,500 pg/ml IL-1β (Wako Pure Chemical Industries, Ltd.) were prepared using a dilution buffer, and the solutions were applied to the plate in an amount of 50 μl/well. After the plate was allowed to stand at room temperature for 60 minutes, the insides of the wells were washed once with a wash buffer. The biotin-labeled secondary antibody (Biolegend) was diluted 500-fold using a dilution buffer, and the resultant was applied to the plate in an amount of 50 μl/well. After the plate was allowed to stand at room temperature for 30 minutes, the insides of the wells were washed once with a wash buffer. Subsequently, HRP-labeled streptavidin (Prozyme) was diluted 4,000-fold (final concentration: 0.25 μg/ml) using a dilution buffer, and the resultant was applied to the plate in an amount of 50 μl/well. After the plate was allowed to stand at room temperature for 30 minutes, the insides of the wells were washed three times with a wash buffer. A chemiluminescent substrate (ImmunoStar LD, Wako Pure Chemical Industries, Ltd.) was applied to the plate in an amount of 30 μl/well, and a chemiluminescence image was obtained using an LAS 4000 mini (GE Health Care). In the end, the chemiluminescence intensity was determined using dedicated software, and the calibration curves as shown in FIG. 6 were prepared (the untreated plate and the conventional plate). The sensitivity of the untreated plate and that of the conventional plate were 9.8 pg/ml and 2.4 pg/ml.

TABLE 1

| 96-well microplates | ELISA | Sensitivity |
|---|---|---|
| Plate of the present invention | Indirect assay | 0.03 ng/ml |
| | Sandwich assay | 0.15 pg/ml |
| Untreated plate | Indirect assay | 3.9 ng/ml |
| | Sandwich assay | 9.8 pg/ml |
| Conventional plate | Indirect assay | 3.9 ng/ml |
| | Sandwich assay | 2.4 pg/ml |

Example 5

The influences of the duration of silanol treatment and the number average molecular weight of the EG chain on the sensitivity of ELISA (indirect assay) were studied. A specific procedure is described below.

Diluted hydrochloric acid (0.35 ml, pH 2.4) was added to 1.65 ml of 3-glycidoxypropyltrimethoxysilane (Momentive Performance Materials Inc.) to prepare silanol. The resultant was added to 100 ml of 2-propanol (Junsei Chemical Co., Ltd.). Further, 0.5 ml of triethylamine (Wako Pure Chemical Industries, Ltd.) was added thereto. The silanol solution was applied to a 96-well microplate (BD Falcon™) in an amount of 100 μl/well. The plate was allowed to stand in such state at room temperature for 60 to 135 minutes. Thereafter, the insides of the wells were washed with pure water and dried by nitrogen blowing. Thus, a primer layer comprising polysiloxane and epoxy groups was formed in the wells of the microplate. Subsequently, EG or PEG (13 types) containing a catalytic amount of concentrated sulfuric acid was applied to the plate in an amount of 100 μl/well. The plate was heated in such state at 80° C. for 45 minutes. Thereafter, the insides of the wells were washed with pure water and dried by nitrogen blowing. Thus, a hydrophilic layer comprising the EG chain was formed on the primer layer. Subsequently, a solvent mixture containing equal weights of anhydrous acetonitrile (Kanto Chemical Co., Inc.) and anhydrous dimethyl sulfoxide (Kanto Chemical Co., Inc.) was used to prepare a solution of CDI (final concentration: 0.5 M; Tokyo Chemical Industry Co., Ltd.), the solution was applied to the plate in an amount of 20 μl/well, and the plate was allowed to stand in such state at room temperature for 30 minutes. Thereafter, the insides of the wells were washed with pure water and dried by nitrogen blowing. Thus, an EG or PEG derivative comprising the (1H-imidazol-1-yl)carbonyl group introduced at an end of the EG chain of the hydrophilic layer was formed. Thus, carriers onto which a substance is to be fixed each having a different binding density of the EG chain and number average molecular weight of the EG chain were obtained. With the use of such carriers onto which a substance is to be fixed, ELISA sensitivity was assayed by the method described in Example 3. As a result, sensitivity that is apparently significantly higher than that of conventional techniques was found to be obtained when the number average molecular weight of the EG chain was 176 or higher, as shown in FIG. 14. When the molecular weight of the EG chain is large, in addition, high sensitivity could be realized at a relatively low density.

The number average molecular weights of raw materials shown in FIG. 14 are as shown below.

TABLE 2

| Number average molecular weights of raw materials | |
|---|---|
| EG | 62 |
| Di EG | 106 |
| Tri EG | 150 |
| Tetra EG | 194 |
| PEG 400 | 380 to 420 |
| PEG 600 | 570 to 630 |
| PEG 1000 | 950 to 1,050 |
| PEG 1540 | 1,300 to 1,600 |
| PEG 2000 | 1,850 to 2,150 |
| PEG 4000 | 2,700 to 3,400 |
| PEG 6000 | 7,300 to 10,200 |
| PEG 10000 | 9,000 to 12,500 |
| PEG 20000 | 15,000 to 25,000 |

Example 6

The influences of the number average molecular weight of EG or PEG on the amount of protein adsorption were studied.

At the outset, a 96-well microplate (not activated) having a hydrophilic layer comprising EG or PEG was produced in the manner described below.

Diluted hydrochloric acid (0.35 ml, pH 2.4) was first added to 1.65 ml of 3-glycidoxypropyltrimethoxysilane (Momentive Performance Materials Inc.) to prepare silanol. The resultant was added to 100 ml of 2-propanol (Junsei Chemical Co., Ltd.). Further, 0.5 ml of triethylamine (Wako Pure Chemical Industries, Ltd.) was added thereto. The silanol solution was applied to a 96-well microplate (BD Falcon™) in an amount of 100 μl/well. The plate was allowed to stand in such state at room temperature for 135 minutes. Thereafter, the insides of the wells were washed with pure water and dried by nitrogen blowing. Thus, a primer layer comprising polysiloxane and epoxy groups was formed in the wells of the microplate. Subsequently, EG or PEG (10 types) containing a catalytic amount of concentrated sulfuric acid was applied to the plate in an amount of 100 μl/well. The plate was heated in such state at 80° C. for 45 minutes. Thereafter, the insides of the wells were washed with pure water and dried by nitrogen blowing. Thus, a hydrophilic layer comprising EG or PEG was formed on the primer layer.

Subsequently, the amount of protein (the HRP-labeled anti-IgG antibody) adsorption to the 96-well microplate having the hydrophilic layer was measured in the manner described below.

Figure 11:
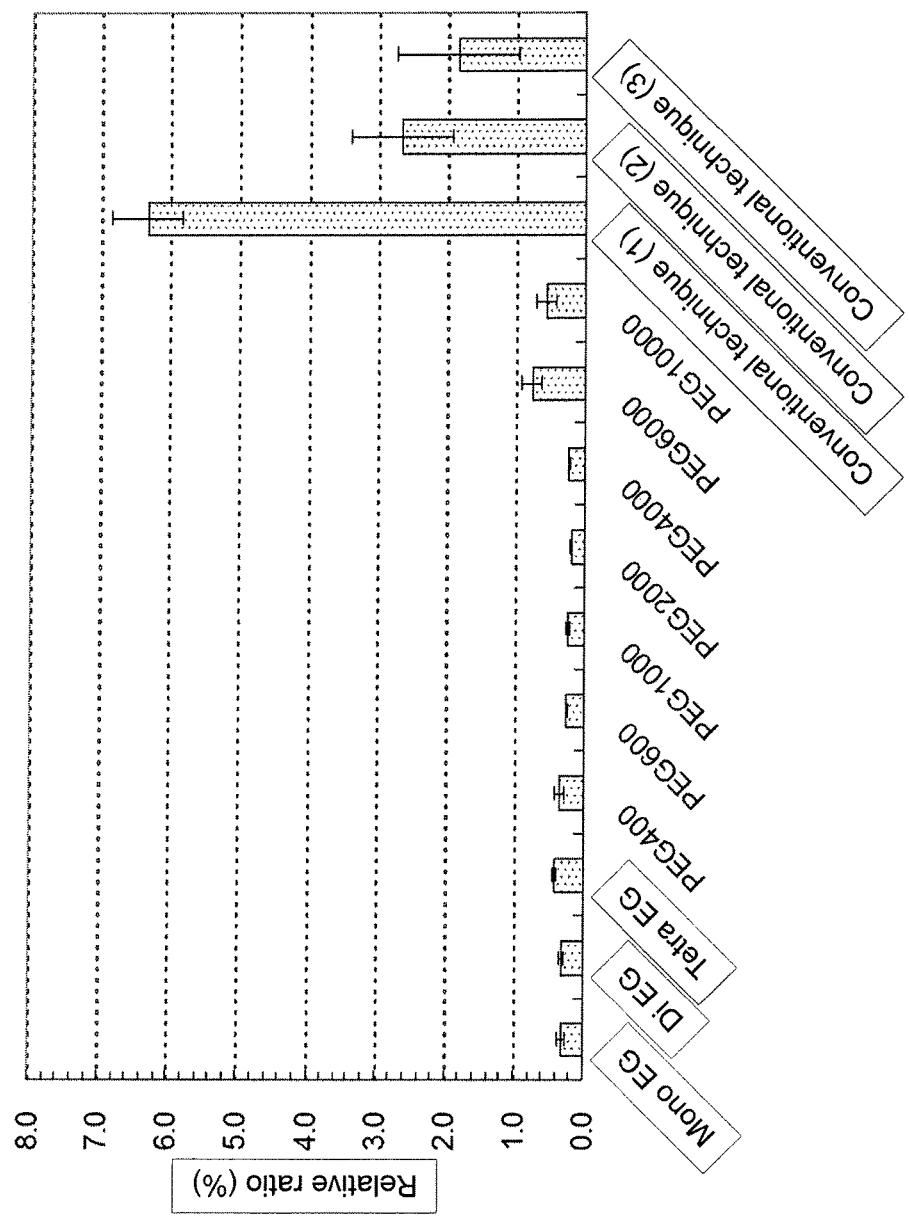
FIG. 11 shows the test results attained in Example 6.

With the use of PBS, a solution of 1 μg/ml HRP-labeled secondary antibody was prepared. The resulting solution was applied to the plate in an amount of 100 μl/well, and the plate was allowed to stand at 4° C. for 24 hours. Thereafter, wells were washed three times with PBS containing 0.05% Tween® 20. Subsequently, a chromogenic reaction solution containing 5 mM SAT-3 (Dojindo Laboratories) and 0.5 mM hydrogen peroxide (Kanto Chemical Co., Inc.) was prepared using PBS. The resulting solution was applied to the plate in an amount of 100 μl/well, and the plate was allowed to stand at room temperature for 15 minutes. Thereafter, 1 N sulfuric acid was added in an amount of 100 μl/well to terminate the chromogenic reaction. In the end, the absorption at 474 nm was assayed using a SpectraMax M2e (Molecular Devices Corporation) (FIG. 11). The value assayed for the untreated 96-well microplate (BD Falcon™) was designated as 100%. As a result, the present invention was found to exert high adsorption-inhibiting effects in a manner substantially independent of the number average molecular weight of PEG, and such inhibitory effects were found to be attained with the use of EG.

Comparative Example 3

The amount of protein adsorption was compared with that of conventional techniques (three types of commercial products). The conventional technique (1) and the conventional technique (2) each use a polystyrene 96-well microplate with an MPC (2-methacryloyloxyethyl phosphorylcholine) polymer layer, while the conventional technique (3) uses a polystyrene 96-well microplate with a PEG layer but without a primer layer. The specific procedure used is as described in Example 6. As a result, the present invention was found to exert higher adsorption-inhibiting effects than conventional techniques (FIG. 11). This is considered to occur because the hydrophilic layer comprising EG or PEG has higher adsorption-inhibiting effects than the MPC polymer layer, and the primer layer increases the EG or PEG binding density.

Example 7

The non-adhesiveness of cells to the 96-well microplate comprising the PEG layer prepared in Example 6 was studied in the manner described below. PEG with a number average molecular weight of 2,700 to 3,400 was used.

Figure 12:
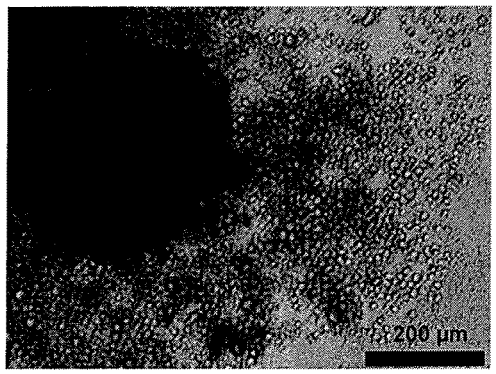
FIG. 12 shows the test results attained in Example 7.
Figure 12:
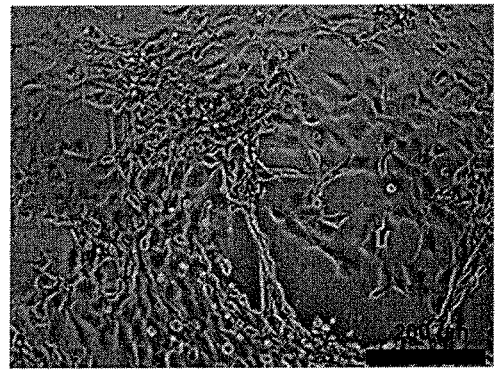

First of all, mouse fibroblasts (CCL163) were suspended in a DMEM medium containing 10% fetal bovine serum, and the resulting suspension was inoculated at a density of $1 \times 10^4$ cells/well. Culture was conducted in an incubator at 37° C. in the presence of 5% $CO_2$ for 8 days, and cellular conditions were then observed using a phase contrast microscope. As a result, adhesion or spreading of cells to the surface of a base material comprising a PEG layer was not observed, and agglutinated masses were formed in a completely suspended state (FIG. 12, left). When culture was conducted under the same conditions using the untreated plate, adhesion, spreading, and growth of cells were apparently observed (FIG. 12, right).

Figure 13:
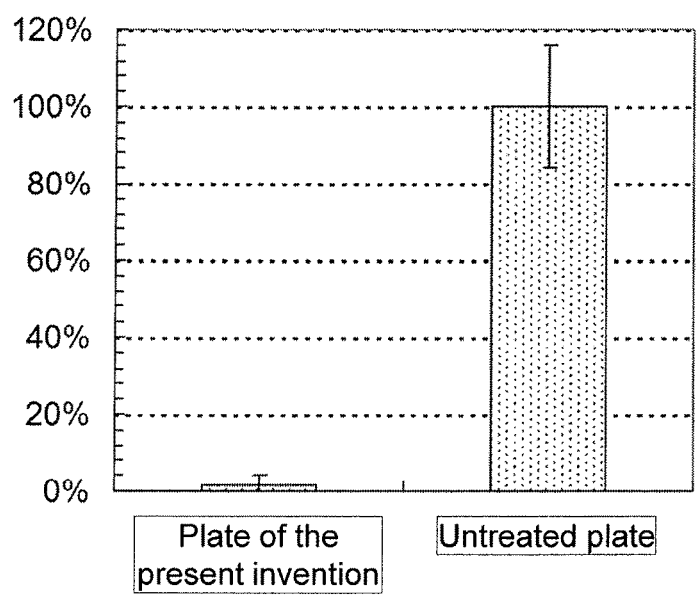
FIG. 13 shows the test results attained in Example 7.

Subsequently, MTS assays were carried out in the manner described below, in order to perform quantitative evaluation of the non-adhesiveness of the cells. At the outset, the cells were cultured under the same conditions, and the medium was subjected to suction to remove non-adhered cells. After the wells were washed once with the medium mentioned above, the medium was applied to the plate in an amount of 100 μl/well. Thereafter, the MTS reagent (CellTiter 96® AQueous One Solution, Promega) was applied to the plate in an amount of 20 μl/well. After the plate was rocked back and forth and left and right for stirring, the plate was allowed to stand in an incubator at 37° C. in the presence of 5% $CO_2$ for 2 hours to develop color. In the end, the absorption of each well was assayed using a SpectraMax M2e (Molecular Devices Corporation). The absorption assayed for the base material having a PEG layer was about 1.3%, relative to the absorption assayed for the untreated plate, which was designated as 100% (FIG. 13). Thus, the base material of the present invention was found to inhibit cell adhesion, spreading, and growth to remarkable degrees.

All publications, patents, and patent applications cited herein are incorporated herein by reference in their entirety.

We claim:

1. A base material comprising at least:
a support containing polystyrene on its surface;
a polysiloxane-containing primer layer on the surface of the support, wherein the polysiloxane-containing primer layer comprises a hydrolyzed form of 3-glycidoxypropyltrimethoxysilane or 3-glycidoxypropyltriethoxysilane and wherein the primer layer is bound to the surface of the support by Van der Waals force or hydrophobic interaction between the polystyrene and 3-glycidoxypropyl groups of the primer layer; and
on the primer layer, a hydrophilic layer containing an ethylene glycol chain with a number average molecular weight from 2,700 to 12,500, wherein one end of the ethylene glycol chain is covalently bound to other 3-glycidoxypropyl groups of the primer layer and the other end of the ethylene glycol chain is bound to a functional group selected from a (1H-imidazol-1-yl) carbonyl group or a succinimidyloxycarbonyl group, wherein the nitrogen concentration in the hydrophilic layer is from 0.010 to 0.050 when the functional group is a succinimidyloxycarbonyl group relative to a carbon concentration resulting from the C—O bonds in the hydrophilic layer being 1 and the nitrogen concentration in the hydrophilic layer is from 0.020 to 0.100 when the functional group is a (1H-imidazol-1-yl) carbonyl group relative to a carbon concentration resulting from the C—O bonds in the hydrophilic layer being 1.

2. A method for producing the base material according to claim 1.

* * * * *